United States Patent [19]

Kemp

[11] Patent Number: 5,447,897
[45] Date of Patent: Sep. 5, 1995

[54] ETHYLENE OXIDE CATALYST AND PROCESS

[75] Inventor: Richard A. Kemp, Stafford, Tex.

[73] Assignee: Shell Oil Company, Houston, Tex.

[21] Appl. No.: 64,287

[22] Filed: May 17, 1993

[51] Int. Cl.$^6$ .................. B01J 23/00; B01J 27/055
[52] U.S. Cl. ...................... 502/303; 502/218; 502/219; 502/220; 502/302; 502/304
[58] Field of Search ............... 502/218, 219, 220, 302, 502/303, 304

[56] References Cited

U.S. PATENT DOCUMENTS

| | | |
|---|---|---|
| 1,325,715 | 8/1963 | Cusumano . |
| 3,316,279 | 4/1967 | Fenton . |
| 3,702,259 | 11/1972 | Nielsen . |
| 3,844,981 | 10/1974 | Cusumano . |
| 3,962,136 | 6/1976 | Nielsen et al. . |
| 3,962,285 | 6/1976 | Cusumano . |
| 3,972,829 | 8/1976 | Michalko . |
| 4,005,049 | 1/1977 | Fields . |
| 4,010,115 | 3/1977 | Nielsen et al. . |
| 4,012,425 | 3/1977 | Nielsen et al. . |
| 4,257,976 | 3/1981 | Pavan et al. . |
| 4,356,312 | 10/1982 | Nielsen et al. . |
| 4,459,372 | 7/1984 | Arena . |
| 4,536,482 | 8/1985 | Carcia . |
| 4,548,921 | 10/1985 | Geus et al. . |
| 4,761,394 | 8/1988 | Lauritzen . |
| 4,766,105 | 8/1988 | Lauritzen . |
| 4,808,738 | 2/1989 | Laurtizen . |
| 4,908,343 | 3/1990 | Bhasin . |
| 5,051,395 | 9/1991 | Mitchell et al. ............... 502/348 |
| 5,112,795 | 5/1992 | Minahan et al. ............... 502/347 |

FOREIGN PATENT DOCUMENTS

| | | |
|---|---|---|
| 0011356 | 9/1979 | European Pat. Off. . |
| 0266015 | 10/1987 | European Pat. Off. . |
| 0480537 | 10/1991 | European Pat. Off. . |
| 0496470 | 1/1992 | European Pat. Off. . |
| 94201334 | 8/1994 | European Pat. Off. . |
| 4363139 | 6/1991 | Japan . |
| 1371685 | 7/1972 | United Kingdom . |

Primary Examiner—Asok Pal
Assistant Examiner—E. D. Irzinski
Attorney, Agent, or Firm—Pamela J. McCollough

[57] ABSTRACT

This invention relates to an ethylene oxide catalyst having improved selectivity stability which catalyst comprises silver, a promoting amount of alkali metal, a promoting amount of rare earth, a promoting amount of rhenium and, optionally, a promoting amount of rhenium co-promoter selected from sulfur, molybdenum, tungsten, chromium and mixtures thereof, supported on a porous refractory support.

84 Claims, No Drawings

ETHYLENE OXIDE CATALYST AND PROCESS

FIELD OF THE INVENTION

The invention relates to silver-containing catalysts suitable for the preparation of ethylene oxide and to the use of the catalysts for the preparation of ethylene oxide.

BACKGROUND OF THE INVENTION

Catalysts for the production of ethylene oxide from ethylene and molecular oxygen are generally supported silver catalysts. Such catalysts are typically promoted with alkali metals. The use of small amounts of the alkali metals potassium, rubidium and cesium were noted as useful promoters in supported silver catalysts in U.S. Pat. No. 3,962,136, issued Jun. 8, 1976, and U.S. Pat. No. 4,010,115, issued Mar. 1, 1977. The use of other co-promoters, such as rhenium, or rhenium along with sulfur, molybdenum, tungsten and chromium is disclosed in U.S. Pat. No. 4,766,105, issued Aug. 23, 1988, and U.S. Pat. No. 4,808,738, issued Feb. 28, 1989. U.S. Pat. No. 4,908,343, issued Mar. 13, 1990, discloses a supported silver catalyst containing a mixture of a cesium salt and one or more alkali metal and alkaline earth metal salts.

U.S. Pat. No. 3,844,981 issued Oct. 29, 1974, U.S. Pat. No. 3,962,285 issued Jun. 8, 1976 and British Patent No. 1,325,715, published Aug. 8, 1973, disclose the use of silver-rhenium ethylene oxide catalysts. In these patents a high surface area silver derivative such as silver oxide is impregnated with a rhenium solution and subsequently reduced to provide metallic rhenium alloyed with the silver. The '285 patent discloses the use of KOH to precipitate $Ag_2O$ from $AgNO_3$. There is no disclosure in the patents of the use of suitable inert supports such as porous refractory supports. U.S. Pat. 4,548,921, issued Oct. 22, 1985, discloses the use of rhenium in silver-supported ethylene oxide catalysts. In this reference, the rhenium is first placed on the support in the form of finely divided metal particles and the silver is subsequently deposited on the outer surface of the particles. U.S. Pat. No. 3,316,279, issued Apr. 25, 1967, discloses the use of rhenium compounds, particularly ammonium and alkali metal perrhenates for the oxidation of olefins to olefin oxides. In this reference, however, the rhenium compounds are used, unsupported, along with a reaction modifier (cyanides, pyridines or quinolines) in a liquid phase reaction. U.S. Pat. No. 3,972,829, issued Aug. 3, 1976, discloses a method for distributing catalytically active metallic components on supports using an impregnating solution of catalyst precursor compound and an organic thioacid or a mercaptocarboxylic acid. Catalytically active metals include metals of Groups IVA, IB, VIB, VIIB and VIII, including rhenium and which may be in either the oxidized or reduced state. However, promoting amounts of rare earth in combination with silver and promoter amounts of alkali metal and rhenium on a porous refractory support are not suggested. U.S. Pat. No. 4,459,372, issued Jul. 10, 1984, discloses the use of rhenium metal in combination with a surface metallated (using Ti, Zr, Hf, V, Sb, Pb, Ta, Nb, Ge and/or Si) alumina or silica. U.S. Pat. No. 4,005,049, issued Jan. 25, 1977, teaches the preparation of a silver/transition metal catalyst useful in oxidation reactions. In this instance, the silver serves as both a catalyst and a support for the transition metal co-catalyst. In U.S. Pat. No. 4,536,482, issued Aug. 20, 1985, catalytically active metals such as Ag and Re are co-sputtered along with a co-sputtered support material on a particular support. U.S. Pat. No. 4,257,976, issued Mar. 24, 1981, discloses a catalyst combination of reduced silver, a carbonate of a rare earth metal and yttrium, a salt of an alkali or alkaline earth metal and a catalyst carrier. None of these references disclose the use of a promoting amount of rare earth which is present on a silver-based, alkali metal/rhenium-doped supported catalyst.

SUMMARY OF THE INVENTION

The invention relates to a catalyst for the production of ethylene oxide catalyst from ethylene and molecular oxygen in the vapor phase which catalyst comprises a catalytically effective amount of silver, a promoting amount of alkali metal, a promoting amount of a rare earth metal compound, a promoting amount of rhenium and optionally, a rhenium co-promoter selected from sulfur, molybdenum, tungsten, chromium and mixtures thereof supported on a porous, refractory support.

It has been found that catalysts containing a promoting amount of rare earth compound have higher selectivity stabilities than those obtained with catalysts containing no rare earth compound.

DESCRIPTION OF THE PREFERRED EMBODIMENTS

Generally, in the vapor phase reaction of ethylene with oxygen to produce ethylene oxide, the ethylene is present in at least a double amount (on a molar basis) compared with oxygen, but frequently is often much higher. Therefore, the conversion is calculated according to the mole percentage of oxygen which has been consumed in the reaction to form ethylene oxide and any oxygenated by-products. The oxygen conversion is dependent on the reaction temperature, and the reaction temperature is a measure of the activity of the catalyst employed. The value $T_{40}$ indicates the temperature at 40 mole percent oxygen conversion in the reactor and the value T is expressed in °C. This temperature for any given catalyst is higher when the conversion of oxygen is higher. Moreover, this temperature is strongly dependent on the employed catalyst and the reaction conditions. The selectivity (to ethylene oxide) indicates the molar amount of ethylene oxide in the reaction product compared with the total molar amount of ethylene converted. In this specification, the selectivity is indicated as $S_{40}$, which means the selectivity at 40 mole percent oxygen conversion. The selectivity of silver-based ethylene oxide catalysts can and will decrease over a period of time of usage. Therefore, from an economic and practical standpoint, it is not only the initial selectivity of a catalyst which is important, but also the rate at which the selectivity declines. In fact, significant improvement in lowering the decline rate of a catalyst can prove more economically attractive than a high initial selectivity. Thus, the rate at which a catalyst loses selectivity is a predominant factor influencing the efficiency of any particular catalyst, and lowering this decline rate can lead to significant savings in terms of minimizing waste of the ethylene starting material. As used herein, "selectivity" is used to refer to the selectivity of ethylene oxide catalysts when measured at a given constant oxygen conversion level of 40% at a gas hourly space velocity of approximately 3300 and when measured after the catalyst has been placed on stream for at least several days.

The catalysts of the instant invention comprise a catalytically effective amount of silver, a promoting amount of alkali metal, a promoting amount of a rare earth compound, a promoting amount of rhenium and, optionally, a promoting amount of a rhenium co-promoter selected from sulfur, chromium, molybdenum, tungsten and mixtures thereof, supported on a porous, refractory support.

In general, the catalysts of the present invention are prepared by impregnating porous refractory supports with silver ions or compound(s), complex(es) and/or salt(s) dissolved in a suitable solvent sufficient to cause deposition on the support of from about 1 to about 25 percent by weight, basis the weight of the total catalyst, of silver. The impregnated support is then separated from the solution and the deposited silver compound is reduced to metallic silver. Also deposited on the support either prior to, coincidentally with, or subsequent to the deposition of the silver will be suitable ions, or compound(s) and/or salt(s) of alkali metal dissolved in a suitable solvent. Also deposited on the carrier coincidentally with the deposition of the silver and/or alkali metal will be suitable rare earth compound(s), complex(es) and/or salt(s) dissolved in an appropriate solvent. Also deposited on the support either prior to, coincidentally with, or subsequent to the deposition of the silver and/or alkali metal and/or rare earth will be suitable rhenium ions or compound(s), complex(es) and/or salt(s) dissolved in an appropriate solvent. In a preferred embodiment, suitable ions or salt(s), complex(es) and/or compound(s) of sulfur, molybdenum, tungsten and/or chromium dissolved in an appropriate solvent will be deposited on the carrier either prior to, coincidentally with, or subsequent to the deposition of the silver and/or alkali metal and/or rare earth and/or rhenium.

The carrier or support employed in these catalysts in its broadest aspects can be any of the large number of conventional, porous refractory catalyst carriers or support materials which are considered relatively inert in the presence of ethylene oxidation feeds, products and reaction conditions. Such conventional materials are known to those skilled in the art and may be of natural or synthetic origin and preferably are of a macroporous structure, i.e., a structure having a surface area below about 10 $m^2/g$ and preferably below about 3 $m^2/g$. Particularly suitable supports are those of aluminous composition. Examples of supports which have been used as supports for different catalysts and which could, it is believed, be used as supports for ethylene oxide catalysts are the aluminum oxides (including the materials sold under the trade name "Alundum"), charcoal, pumice, magnesia, zirconia, keiselguhr, fuller's earth, silicon carbide, porous agglomerates comprising silica and/or silicon carbide, silica, magnesia, selected clays, artificial and natural zeolites and ceramics. Refractory supports especially useful in the preparation of catalysts in accordance with this invention comprise the aluminous materials, in particular those comprising alpha alumina. In the case of alpha alumina-containing supports, preference is given to those having a specific surface area as measured by the B.E.T. method of from about 0.03 $m^2/g$ to about 10 $m^2/g$, preferably from about 0.05 $m^2/g$ to about 5 $m^2/g$, more preferably from about 0.1 $m^2/g$ to about 3 $m^2/g$, and a water pore volume as measured by conventional water absorption techniques of from about 0.1 to about 0.75 cc/g by volume. The B.E.T. method for determining specific surface area is described in detail in Brunauer, S., Emmet, P. Y. and Teller, E., *J. Am. Chem. Soc.*, 60, 309–16 (1938).

Certain types of alpha alumina containing supports are particularly preferred. These alpha alumina supports have relatively uniform pore diameters and are more fully characterized by having B.E.T. specific surface areas of from about 0.1 $m^2/g$ to about 3 $m^2/g$, preferably from about 0.1 $m^2/g$ to about 2 $m^2/g$, and water pore volumes of from about 0.10 cc/g to about 0.55 cc/g. Typical properties of some supports found particularly useful in the present invention are presented in Table I. Suitable manufacturers of carriers comparable to those in Table I include Norton Company and United Catalysts, Inc. (UCI).

TABLE I

| Carrier | A | B | C | D | E | F |
|---|---|---|---|---|---|---|
| B.E.T. Surface Area, $m^2/g^{(a)}$ | 0.21 | 0.42 | 0.51 | 0.48 | 0.57 | 2.06 |
| Water Pore Volume, cc/g | 0.26 | 0.36 | 0.38 | 0.49 | 0.44 | 0.65 |
| Crush Strength, FPCS, lbs$^{(b)}$ | 100% 20 lbs | 97% 15 | 21 | 14 | 15 | No Data |
| Total Pore Volume, Hg, cc/g$^{(c)}$ | 1.26 | 0.42 | 0.40 | 0.46 | 0.42 | 0.65 |
| Average Pore Diameter, Hg, Å$^{(c)}$ | 620 | 560 |  | 550 | 770 | 1000 |
| Median Pore Diameter, Hg, microns$^{(c,e)}$ | 3.7 | 2.7 | 3.5 | 3.4 | 2.4 | 2.5 |
| Percent Pore Volume in Pores Greater Than 350Å$^{(c)}$ | 90.0% | 88.5% | 93.0% | 89.1% | 91.5% | 94.1% |
| Percent Pore Volume in Pores Greater Than 1 Micron$^{(c)}$ | 87.0% | 82.5% | 77.0% | 82.3% | 83.5% | 61.0% |
| % Wt. Alpha Alumina | 99.5 | 98 | 98.8 | 98.5 | 98 | 70–75 |
| Water Leachable Na, ppmw | 12 | 53 | 69 | 24 | 18 | No Data |
| Acid-Leachable Na, ppmw | 40 | 96 | 188 | 51 | 45 | No Data |
| Water Leachable K, ppmw | 5 | 22 | 32 | 22 | 10 | No Data |
| Acid-Leachable Fe, ppmw | 2 | 5 | No Data | 1 | 5 | No Data |
| % Wt. $SiO_2$ | .5 | 2 | 0.1 | 15 | 2 | 25–30 |

$^{(a)}$Method of Brunauer, Emmet and Teller, loc. cit.
$^{(b)}$Flat Plate Crush Strength, single pellet.
$^{(c)}$Determined by mercury intrusion to 55,000 psia using Micrometrics Autopore 9200 or 9210 (130° Contact angle, 0.473 N/m surface tension of Hg).
$^{(e)}$Median pore diameter represents the pore diameter wherein 50% of the total pore volume is found in pores having less than (or greater than) the median pore diameter.

Of the carriers listed in TABLE I, B and C are preferred because they provide catalysts which have high initial selectivities.

The support, irrespective of the character of the support or carrier used, is preferably shaped into particles, chunks, pieces, pellets, rings, spheres, wagon wheels, and the like of a size suitable for use in fixed bed reactors. Conventional commercial fixed bed reactors are typically in the form of a plurality of parallel elongated tubes (in a suitable shell) approximately 0.7 to 2.7 inches O.D. and 0.5 to 2.5 inches I.D. and 15-45 feet long filled with catalyst. In such reactors, it is desirable to use a support formed into a rounded shape, such as, for example, spheres, pellets, rings, tablets and the like, having diameters from about 0.1 inch to about 0.8 inch.

Particular supports having differing properties such as surface area and pore volume may be selected in order to provide particular catalytic properties. With regard to surface area (B.E.T.), a possible lower limit is about 0.01 $m^2/g$ and a possible upper limit is about 10 $m^2/g$. With regard to water pore volume, a possible lower limit is about 0.05 cc/g and a possible upper limit is about 0.8 cc/g.

The catalysts of the present invention are prepared by a technique in which the alkali metal promoters, the rare earth compound, the rhenium, and the rhenium co-promoter, if present, in the form of soluble salts and/or compounds are deposited on the catalyst and/or support prior to, simultaneously with, or subsequent to the deposition of the silver and each other. The alkali metals may be deposited at one step of the process and the rare earth, rhenium and/or the rhenium co-promoter, if present, at a different step or steps. The preferred method is to deposit silver, alkali metal, rare earth, rhenium and rhenium co-promoter simultaneously on the support, that is, in a single impregnation step, although it is believed that the individual or concurrent deposition of the alkali metal, rare earth, rhenium and rhenium co-promoter, if present, prior to and/or subsequent to the deposition of the silver would also produce suitable catalysts.

Promoting amounts of alkali metal or mixtures of alkali metal are deposited on a porous support using a suitable solution. Although alkali metals exist in a pure metallic state, they are not suitable for use in that form. They are used as ions or compounds of alkali metals dissolved in a suitable solvent for impregnation purposes. The carrier is impregnated with a solution of alkali metal promoter ions, salt(s) and/or compound(s) before, during or after impregnation of the silver ions or salt(s), complex(es), and/or compound(s) has taken place. An alkali metal promoter may even be deposited on the carrier after reduction to metallic silver has taken place. The promoting amount of alkali metal utilized will depend on several variables, such as, for example, the surface area and pore structure and surface chemical properties of the carrier used, the silver content of the catalyst and the particular ions used in conjunction with the alkali metal cation, rare earth or rhenium or rhenium co-promoter, if present, and the amounts of rare earth, rhenium and rhenium co-promoter, if any, present. The amount of alkali metal promoter deposited upon the support or present on the catalyst generally lies between about 10 parts per million and about 3000 parts per million, preferably between about 15 parts per million and about 2000 parts per million and more preferably, between about 20 parts per million and about 1500 parts per million by weight of total catalyst. Most preferably, the amount ranges between about 50 parts per million and about 1000 parts per million by weight of the total catalyst. The degree of benefit obtained within the above-defined limits will vary depending upon particular properties and characteristics, such as, for example, reaction conditions, catalyst preparative techniques, surface area and pore structure and surface chemical properties of the carrier utilized, silver content of the catalyst, and other compounds, cations or anions present in addition to alkali metal ions such as ions added with the alkali metal, rare earth, rhenium and rhenium co-promoter, if present, or compounds remaining from the impregnating solution, and the above-defined limits were selected to cover the widest possible variations in properties and characteristics. The effects of these variation in properties are readily determined by experimentation. The alkali metal promoters are present on the catalysts in the form of cations (ions) or compounds of complexes or surface compounds or surface complexes rather than as the extremely active free alkali metals, although for convenience purposes in this specification and claims they are referred to as "alkali metal" or "alkali metal promoters" even though they are not present on the catalyst as metallic elements. For purposes of convenience, the amount of alkali metal deposited on the support or present on the catalyst is expressed as the metal. Without intending to limit the scope of the invention, it is believed that the alkali metal compounds are oxidic compounds. More particularly, it is believed that the alkali metal compounds are probably in the form of mixed surface oxides or double surface oxides or complex surface oxides with the aluminum of the support and/or the silver of the catalyst, possibly in combination with species contained in or formed from the reaction mixture, such as, for example, chlorides or carbonates or residual species from the impregnating solution(s).

In a preferred embodiment, at least a major proportion (greater than 50%) of the alkali metals are selected from the group consisting of lithium, sodium, potassium, rubidium, cesium, and mixtures thereof. As used herein, the term "alkali metal" and cognates thereof refers to the alkali metals selected from the group consisting of lithium, sodium, potassium, rubidium, cesium and mixtures thereof. As used herein, the term "mixtures of alkali metals" or cognates of these terms refers to the use of two or more of the alkali metals, as appropriate, to provide a promoting effect. Non-limiting examples include cesium plus rubidium, cesium plus potassium, cesium plus sodium, cesium plus lithium, cesium plus rubidium plus sodium, cesium plus potassium plus sodium, cesium plus lithium plus sodium, cesium plus rubidium plus potassium plus sodium, cesium plus rubidium plus potassium plus lithium, cesium plus potassium plus lithium and the like. A preferred alkali metal promoter is cesium. A particularly preferred alkali metal promoter is cesium plus at least one additional alkali metal. The additional alkali metal is preferably selected from sodium, lithium and mixtures thereof, with lithium being preferred.

It should be understood that the amounts of alkali metal promoters on the catalysts are not necessarily the total amounts of these metals present in the catalyst. Rather, they are the amounts of alkali metal promoters which have been added to the catalyst by impregnation with a suitable solution of ions, salts and/or compounds and/or complexes of alkali metals. These amounts do not include amounts of alkali metals which are locked into the support, for example, by calcining, or are not extractable in a suitable solvent such as water or lower alkanol or amine or mixtures thereof and do not provide a promoting effect. It is also understood that a source of the alkali metal promoter ions, salts and/or compounds used to promote the catalyst may be the carrier. That is, the carrier may contain extractable amounts of alkali metal that can be extracted with a suitable solvent, such as water or lower alkanol, thus preparing an impregnating solution from which the alkali metal ions, salts and/or compounds are deposited or redeposited on the support.

As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counterions. The term "oxidic" refers to a charged or neutral species wherein an element in question is bound to oxygen and possibly one or more different elements by surface and/or chemical bonding, such as ionic and/or covalent and/or coordinate bonding. Thus, an oxidic compound is an oxygen-containing compound which also may be a mixed, double or complex surface oxide. Illustrative oxidic compounds include, by way of non-limiting examples, oxides (containing only oxygen as the second element), hydroxides, nitrates, sulfates, carboxylates, carbonates, bicarbonates, oxyhalides, etc. as well as surface species wherein the element in question is bound directly or indirectly to an oxygen either in the substrate or the surface.

As used herein, the term "promoting amount" of a certain component of a catalyst refers to an amount of that component which works effectively to provide an improvement in one or more of the catalytic properties of that catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced and may even be diminished. It is further understood that different catalytic properties may be enhanced at different operation conditions. For example, a catalyst having enhanced selectivity at one set of operating conditions may be operated at a different set of conditions wherein the improvement shows up in the activity rather that the selectivity and an operator of an ethylene oxide plant will intentionally change the operation conditions in order to take advantage of certain catalytic properties even at the expense of other catalytic properties in order to maximize profits by taking into account feedstock costs, energy costs, by-product removal costs and the like. The particular combination of silver, support, rare earth promoter, alkali metal promoter, rhenium promoter and optionally, rhenium co-promoter of the instant invention will provide an improvement in one or more catalytic properties over the same combination of silver, support, alkali metal promoter, rhenium promoter and optionally, rhenium co-promoter and no rare earth promoter.

As used herein, the term "catalytically effective amount of silver" refers to an amount of silver that provides a measurable conversion of ethylene and oxygen to ethylene oxide.

Promoting amounts of rare earth compounds or mixtures of rare earth compounds are also deposited on the carrier. Although rare earth metals exist in a pure metallic state, they are not suitable for use in that form. They are used as ions or compounds of rare earth metals dissolved in a suitable solvent for impregnation purposes. The carrier is impregnated with a solution of rare earth promoter ions, salt(s) and/or compound(s) before, during or after impregnation of the silver ions or salt(s), complex(es), and/or compound(s) has taken place. A rare earth promoter may even be deposited on the carrier after reduction to metallic silver has taken place, or before, during or after impregnation of the rare earth ions, salt(s) and/or compound(s) has taken place. The promoting amount of rare earth utilized will depend on several variables, such as, for example, the surface area and pore structure and surface chemical properties of the carrier used, the silver content of the catalyst and the particular ions used in conjunction with the alkali metal cation, rare earth or rhenium or rhenium co-promoter, if present, and amounts of rare earth, rhenium and rhenium co-promoter, if any, present. The amount of rare earth promoter deposited upon the support or present on the catalyst generally lies between about 10 parts per million and about 1000 parts per million, and preferably between about 15 parts per million and about 500 parts per million by weight of the total catalyst. Most preferably, the amount ranges between about 30 parts per million and about 250 parts per million by weight of the total catalyst. The promoting effect provided by the rare earth will vary depending upon particular properties and characteristics, such as, for example, reaction conditions, catalyst preparative techniques, surface area and pore structure and surface chemical properties of the carrier utilized, the silver, alkali metal, rhenium and rhenium co-promoter content of the catalyst, and other compounds, cations or anions present in addition to those containing the alkali metal, rare earth, rhenium and rhenium co-promoter, if present, or compounds remaining from the impregnating solution, and the above-defined limits were selected to cover the widest possible variations in properties and characteristics. The effects of these variations in properties are readily determined by experimentation. The rare earth promoter or promoters are presumably present on the catalyst in the form of oxides or oxygen-bound species, or surface compounds or surface complexes rather than as metals, although for purposes of convenience in this specification and claims, they are referred to as "rare earth(s)" "rare earth metal(s)", "rare earth metal compound (s)", "rare earth compound(s)", and/or "rare earth promoters" even though they are not present on the catalyst as metals. For purposes of convenience, the amount of rare earth deposited on the support or present on the catalyst is expressed as the metal rather than in the cationic or compounds or complexes or surface compounds or surface complexes. Without intending to limit the scope of the invention, it is believed that the rare earth metal compounds are oxidic compounds. More particularly, it is believed that the rare earth metal compounds are probably in the form of mixed surface oxides or double surface oxides or complex surface oxides with the aluminum of the support and/or the silver of the catalyst, possibly in combination with species contained in or formed from the reaction mixture, such as, for example, chlorides or carbonates or residual species from the impregnating solution(s).

As used herein, the terms "rare earth metal" and "rare earth" refer to the rare earth metals or elements having atomic numbers 58 through 71 in the Periodic Table of the Elements i.e., cerium, praseodymium, neodymium, promethium, samarium, europium, gadolinium, terbium, dysprosium, holmium, erbium, thulium, ytterbium, and lutetium. As used herein, the term "mixtures of rare earth metals" refers to the use of two or more of the rare earth metals having atomic numbers 58 through 71 in the Periodic Table of the Elements, as appropriate, to provide a promoting effect.

In a preferred embodiment, the rare earth metal is selected from the group consisting of cerium, neodymium, samarium, gadolinium, dysprosium, erbium, ytterbium, and mixtures thereof, with cerium, neodymium, gadolinium, ytterbium, and mixtures thereof being particularly preferred. Particularly preferred rare earth promoters are gadolinium, cerium and ytterbium. It should be understood that the use of Markush terminology in this specification and claims to indicate the rare earth metals cerium and/or neodymium and/or samarium and/or gadolinium and/or dysprosium and/or erbium and/or ytterbium is not meant and does not exclude the presence, inclusion or the use of the remainder of the rare earth metals having atomic numbers 58 through 71 in the Periodic Table of the Elements. Thus, the use of a Markush recitation in the instant specification and claim means that the elements in the recitation are included, but others are not excluded, i.e., the Markush recitation is an open-ended recitation.

The promoting effect provided by the rare earth compound can be affected by a number of variables such as for example, reaction conditions, catalyst preparative techniques, surface area and pore structure and surface chemical properties of the support, the silver, alkali metal, rhenium and, if present, rhenium co-promoter content of the catalyst, and the presence of other cations and anions present on the catalyst alone or in combination with the alkali metal and/or rare earth and/or rhenium and/or rhenium co-promoter. The presence of other activators, stabilizers, promoters, enhancers or other catalyst improvers can also affect the promoting effects of the rare earth. It is understood that any supported silver-based, alkali metal/rhenium promoted ethylene oxide catalyst which contains other cations and/or anions or any other activators, promoters, enhancers, stabilizers or the catalyst improvers and which contains an amount of rare earth which provides a promoting effect, more preferably which provides higher selectivity stabilities than those obtained under the same reaction conditions with the same catalyst which contains no rare earth promoter, will fall within the scope of the instant invention and claims.

The carrier is also impregnated with rhenium ions, salt(s), compound(s), and/or complex(es). This may be done at the same time that the alkali metal promoter is added, or before or later; or at the same time the rare earth promoter is added, or before or later; or at the same time that the silver is added, or before or later; or at the same time that the rhenium co-promoter, if present, is added, or before or later. Preferably, rhenium, rare earth, alkali metal, rhenium co-promoter, if present, and silver are in the same impregnating solution, although it is believed that their presence in different solutions will still provide suitable catalysts. The preferred amount of rhenium, calculated as the metal, deposited on or present on the carrier or catalyst ranges from about 0.1 micromoles per gram to about 10 micromoles per gram, more preferably from about 0.2 micromoles per gram to about 5 micromoles per gram of total catalyst, or, alternatively stated, from about 19 parts per million to about 1860 parts per million, preferably from about 37 parts per million to about 930 parts per million by weight of total catalyst. The degree of benefit obtained within the above-defined limits will vary depending upon particular properties and characteristics, such as, for example, reaction conditions, catalyst preparative conditions, surface area and pore structure and surface chemical properties of the carrier utilized, silver content of the catalyst and other compounds, anions or cations present in addition to those containing rhenium, alkali metal, rare earth, or rhenium co-promoter, such as ions added with the alkali metal, rare earth, rhenium or rhenium co-promoter, or compounds remaining from the impregnating technique, and the above-defined limits were selected to cover the widest possible variations in properties and characteristics. The effects of these variations are readily determined by experimentation. For purposes of convenience, the amount of rhenium present on the catalyst is expressed as the metal, irrespective of the form in which it is present.

The rhenium compounds used in the preparation of the instant catalysts are rhenium compounds that can be solubilized in an appropriate solvent. Preferably, the solvent is a water-containing solvent. More preferably, the solvent is the same solvent used to deposit the silver and the alkali metal promoter. Examples of suitable rhenium compounds include the rhenium salts such as rhenium halides, the rhenium oxyhalides, the rhenates, the perrhenates, the oxides and the acids rhenium. A preferred compound for use in the impregnation solution is the perrhenate, preferably ammonium perrhenate. However, the alkali metal perrhenates, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, i.e., $ReO_4$. It is also understood that there are many rhenium compounds that are not soluble per se in water. However, these compounds can be solubilized by utilizing various acids, bases, peroxides, alcohols, and the like. After solubilization, these compounds could be used, for example, with an appropriate amount of water or other suitable solvent to impregnate the carriers. Of course, it is also understood that upon solubilization of many of these compounds, the original compound no longer exists after solubilization. For example, rhenium metal is not soluble in water. However, it is soluble in concentrated nitric acid as well as in hydrogen peroxide solution. Thus, by using an appropriate reactive solvent, one could use rhenium metal to prepare a solubilized rhenium-containing impregnating solution. In a preferred embodiment of the instant invention, the rhenium present on the catalyst is present in a form that is extractable in a dilute aqueous base solution.

It was found in U.S. Pat. No. 4,766,105, issued Aug. 23, 1988, that if a rhenium co-promoter is added to an alkali metal/rhenium doped supported silver catalyst, an improvement in initial selectivity is obtained. While suitable catalysts can be prepared in the absence of a rhenium co-promoter, it is preferable that the catalyst in the present invention contain a rhenium co-promoter. When a co-promoter is utilized, the co-promoter is a selected from the group consisting of sulfur, molybdenum, tungsten, chromium and mixtures thereof, preferably a compound of sulfur, molybdenum, tungsten, chromium and mixtures thereof. The exact form of the co-promoter on the catalyst is not known. The co-promoter, it is believed, is not present on the catalyst in the elemental form since the co-promoter is applied to catalyst in the form of ions, salts, compounds and/or complexes and the reducing conditions generally used to reduce the silver to metallic silver are not usually sufficient to reduce the sulfur, molybdenum, tungsten or chromium to the elemental form. It is believed that the co-promoter deposited on the support or present on the catalyst is in the compound form, and probably in the form of an oxygen-containing or oxidic compound. In a presently preferred embodiment, the co-promoter is applied to the catalyst in the oxyanionic form, i.e, in the form of an anion, or negative ion which contains oxygen. Examples of anions of sulfur that can be suitably applied include sulfate, sulfite, bisulfite, bisulfate, sulfonate, persulfate, thiosulfate, dithionate, etc. Preferred compounds to be applied are ammonium sulfate and the alkali metal sulfates. Examples of anions of molybdenum, tungsten and chromium that can be suitably applied include molybdate, dimolybdate, paramolybdate, other iso- and hetero-polymolybdates, etc.; tungstate, paratungstate, metatungstate, other iso- and heteropolytungstates, etc.; and chromate, dichromate, chromite, halochromate, etc. Preferred are sulfates, molybdates, tungstates and chromates. The anions can be supplied with various counter-ions. Preferred are ammonium, alkali metal and hydrogen (i.e. acid form). The anions can be prepared by the reactive dissolution of various non-anionic materials such as the oxides such as $SO_2$, $SO_3$, $MoO_3$, $WO_3$, $Cr_2O_3$, etc., as well as other materials such as halides, oxyhalides, hydroxyhalides, hydroxides, sulfides, etc., of the metals.

When a co-promoter is used, the carrier is impregnated with rhenium co-promoter ions, salt(s), compound(s) and/or complex(es). This may be done at the same time that the other components are added, or before and/or later. Preferably, rhenium co-promoter, rhenium, rare earth, alkali metal and silver are in the same impregnating solution, although it is believed that their presence in different solutions will still provide suitable catalysts.

The preferred amount of co-promoter compound present on or deposited on the support or catalyst ranges from about 0.1 to about 10 micromoles, preferably from about 0.2 to about 5 micromoles, expressed as the element, per gram of total catalyst. The degree of benefit obtained within the above-defined limits will vary depending upon particular properties and characteristics, such as, for example, reaction conditions, catalyst preparative techniques, surface area and pore structure and surface chemical properties of the carrier utilized, silver content of the catalyst, alkali content of the catalyst, rhenium content of the catalyst, and other compounds anions or cations present besides those containing rhenium, rhenium co-promoter and alkali metal, such as ions added with the alkali metal, rhenium or rhenium co-promoter, or compounds remaining from the impregnation technique, and the above-defined limits were selected to cover the widest possible variations in properties and characteristics. These variations are readily determined by experimentation. For purposes of convenience the amount of co-promoter present on the catalyst is expressed as the element irrespective of the form in which it is present.

The presence of the indicated and claimed promoting amount of rhenium co-promoters in this specification and claims does not preclude the use of other activators, promoters, enhancers, stabilizers, improvers, etc., and it is not intended by the use of Markush terminology in this specification and claims to exclude the use of such other activators, promoters, enhancers, stabilizers, improvers, etc.

The co-promoter compounds, salts and/or complexes suitable for use in the preparation of the instant catalysts are compounds, salts and/or complexes which can be solubilized in an appropriate solvent. Preferably, the solvent is a water-containing solvent. More preferably, the solvent is the same solvent used to deposit the silver, alkali metal promoter and rhenium. Preferred co-promoter compounds are the oxyanionic compounds of the co-promoter elements, preferably the ammonium and alkali metal oxyanionates, such as ammonium sulfate, potassium sulfate, cesium chromate, rubidium tungstate, ammonium molybdate, lithium sulfate, sodium tungstate, lithium chromate and the like.

Generally, the carrier is contacted with a silver salt, a silver compound, or a silver complex which has been dissolved in an aqueous solution, so that the carrier is impregnated with said aqueous solution; thereafter the impregnated carrier is separated form the aqueous solution, e.g., by centrifugation or filtration and then dried. The thus obtained impregnated carrier is heated to reduce the silver to metallic silver. It is conveniently heated to a temperature in the range of from about 50° C. to about 600° C., during a period sufficient to cause reduction of the silver salt, compound or complex to metallic silver and to form a layer of finely divided silver, which is bound to the surface of the carrier, both the exterior and pore surface. Air, or other oxidizing gas, reducing gas, an inert gas or mixtures thereof may be conducted over the carrier during this heating step.

There are several known methods to add the silver to the carrier or support. The carrier may be impregnated with an aqueous solution containing silver nitrate dissolved therein, and then dried, after which drying step the silver nitrate is reduced with hydrogen or hydrazine. The carrier may also be impregnated with an ammoniacal solution of silver oxalate or silver carbonate, and then dried, after which drying step the silver oxalate or silver carbonate is reduced to metallic silver by heating, e.g., to about 600° C. Specific solutions of silver salts with solubilizing and reducing agents may be employed as well, e.g., combinations of the vicinal alkanolamines, alkyldiamines and ammonia. One such example of a solution of silver salts comprises an impregnating solution comprising a silver salt of a carboxylic acid, an organic amine alkaline solubilizing/reducing agent, and an aqueous solvent.

Suitable carboxylic acid silver salts include silver carbonate and the silver salts of mono- and polybasic carboxylic and hydrocarboxylic acids of up to about 16 carbon atoms. Silver carbonate and silver oxalate are particularly useful silver salts, with silver oxalate being most preferred.

An organic amine solubilizing/reducing agent is present in the impregnating solution. Suitable organic amine silver-solubilizing/reducing agents include lower alkylenediamines of from 1 to 5 carbon atoms, mixtures of a lower alkanolamine of from 1 to 5 carbon atoms with a lower alkylenediamine of from 1 to 5 carbon atoms, as well as mixtures of ammonia with lower alkanolamines or lower alkylenediamines for from 1 to 5 carbons. Four groups of organic amine solubilizing/reducing agents are particularly useful. The four groups include vicinal alkylenediamines of from 2 to 4 carbon atoms, mixtures of (1) vicinal alkanolamines of from 2 to 4 carbon atoms and (2) vicinal alkylenediamines of from 2 to 4 carbon atoms, mixtures of vicinal alkylenediamines of from 2 to 4 carbon atoms and ammonia, and mixtures of vicinal alkanolamines of from 2 to 4 carbon atoms and ammonia. These solubilizing/reducing agents are generally added in the amount of from about 0.1 to about 10 moles per mole of silver present.

Particularly preferred solubilizing/reducing agents are ethylenediamine, ethylenediamine in combination with ethanolamine, ethylenediamine in combination with ammonia, and ethanolamine in combination with ammonia, with ethylenediamine being most preferred. Ethylenediamine in combination with ethanolamine gives comparable results, but it is believed that impurities present in certain commercially available ethanolamine preparations can produce inconsistent results.

When ethylenediamine is used as the sole solubilizing/reducing agent, it is necessary to add amount of the amine in the range of from about 0.1 to about 5.0 moles of ethylenediamine per mole of silver.

When ethylenediamine and ethanolamine together are used as the solubilizing/reducing agent, it is suitable to employ from about 0.1 to about 3.0 moles of ethylenediamine per mole of silver and from about 0.1 to about 2.0 moles of ethanolamine per mole of silver.

When ethylenediamine or ethanolamine is used with ammonia, it is generally useful to add at least about two moles of ammonia per mole of silver and very suitable to add from about 2 to about 10 moles of ammonia per mole of silver. The amount of ethylenediamine or ethanolamine employed then is suitably from 0.1 to 2.0 moles per mole of silver.

One method of preparing the silver containing catalyst can be found in U.S. Pat. No. 3,702,259, issued Nov. 7, 1972, incorporated by reference herein. Other methods for preparing the silver-containing catalysts which in addition contain higher alkali metal promoters can be found in U.S. Pat. No. 4,010,115, issued Mar. 1, 1977; and U.S. Pat. No. 4,356,312, issued Oct. 26, 1982; U.S. Pat. No. 3,962,136, issued Jun. 8, 1976 and U.S. Pat. No. 4,012,425, issued Mar. 15, 1977, all incorporated by reference herein. Methods for preparing silver-containing catalysts containing higher alkali metal and rhenium promoters can be found in U.S. Pat. No. 4,761,394, issued Aug. 2, 1988, which is incorporated by reference herein, and methods for silver-containing catalysts containing higher alkali metal and rhenium promoters and a rhenium co-promoters can be found in U.S. Pat. No. 4,766,105, issued Aug. 2, 1988, which is incorporated herein be reference.

The preferred amount of alkali metal promoter deposited on or present on the surface of the carrier of catalyst generally lies between about 10 parts per million and about 3000 parts per million, preferably between about 15 parts per million and about 2000 parts per million and more preferably between about 20 parts per million and about 1500 parts per million by weight of alkali metal calculated on the total carrier material. Amounts between about 50 parts per million and about 1000 parts per million are most preferable. Suitable compounds of alkali metals comprise lithium, sodium, potassium, rubidium, cesium or mixtures thereof in a promoting amount with the even more preferred promoters being rubidium and/or cesium plus an additional alkali metal selected from lithium, sodium and mixtures thereof. Preferably the amount ranges from about 10 parts per million and about 3,000 parts per million, more preferably between about 15 parts per million and about 2000 parts per million, even more preferably between about 20 parts per million and about 1500 parts per million by weight, and most preferably between about 50 parts per million and 1000 parts per million by weight. The most preferred promoter is cesium plus lithium, preferably applied in an aqueous solution having cesium nitrate or cesium hydroxide dissolved therein.

There are known excellent methods of applying the promoters coincidentally with the silver on the carrier. Suitable alkali metal salts are generally those which are soluble in the silver-impregnating liquid phase. Besides the above-mentioned compounds may be mentioned the nitrites; the halides, such as fluorides, chlorides, iodides, bromides; oxyhalides; bicarbonates; borates; sulfates; sulfites; bisulfates; acetates; tartrates; lactates and isopropoxides, etc. The use of alkali metal, rare earth, rhenium or co-promoter salts which have ions which react with the silver salt in solution is preferably avoided, e.g. the use of cesium chloride together with silver nitrate in an aqueous solution, since then some silver chloride is prematurely precipitated. Here the use of cesium nitrate is recommended instead of cesium chloride, for example. However, cesium chloride may be used together with a silver salt-amine-complex in aqueous solution, since then the silver chloride is not precipitated prematurely from the solution.

The promoters may be deposited on the carrier (support) or on the catalyst, depending upon the particular impregnation technique or sequence utilized. In this specification and claims, the term "on the catalyst" when referring to the deposition or presence of promoters and/or co-promoters refers to the catalyst which comprises the combination of carrier (support) and silver. Thus, the promoters, i.e., alkali metal, rare earth, rhenium and rhenium co-promoter may be found individually or in a mixture thereof on the catalyst, on the support or on both the catalyst and the support. There may be, for example, alkali, rare earth, rhenium and rhenium co-promoter on the support; alkali metal, rare earth, rhenium and rhenium co-promoter on the catalyst; alkali metal, rare earth, and rhenium on the support and rhenium co-promoter on the catalyst; alkali metal, rare earth, and rhenium co-promoter on the support and rhenium on the catalyst; alkali metal, rare earth, rhenium and rhenium co-promoter on the support and rhenium and rhenium co-promoter on the catalyst and any of the other possible distributions of alkali metal, rare earth, rhenium and/or rhenium co-promoter between the support and/or the catalyst.

The amount of the alkali metal and/or rare earth and/or rhenium promoters and/or rhenium co-promoters on the porous carrier or catalyst may also be regulated within certain limits by washing out the surplus of promoter material with an appropriate solvent, for example, methanol or ethanol.

A particularly preferred process of impregnating the carrier consists of impregnating the carrier with an aqueous solution containing a silver salt of a carboxylic acid, an organic amine, a salt of cesium, ammonium perrhenate and ammonium sulfate dissolved therein. Silver oxalate is a preferred salt. It can be prepared by reacting silver oxide (slurry in water) with (a) a mixture of ethylenediamine and oxalic acid, or (b) oxalic acid and then ethylenediamine, which latter is preferred, so that an aqueous solution of silver oxalate-ethylenediamine complex is obtained, to which solution is added a certain amount of cesium compound, ammonium perrhenate and ammonium sulfate. While addition of the amine to the silver oxide before adding the oxalic acid is possible, it is not preferred since it can give rise to solutions which are unstable or even explosive in nature. Other diamines and other amines, such as ethanolamine, may be added as well. A cesium-containing silver oxalate solution may also be prepared by precipitating silver oxalate from a solution of cesium oxalate and silver nitrate and rinsing with water or alcohol the obtained silver oxalate in order to remove the adhering cesium salt until the desired cesium content is obtained. The cesium-containing silver oxalate is then solubilized with ammonia and/or an amine in water and ammonium perrhenate and ammonium sulfate is added. Rubidium-, potassium-, sodium-, lithium- and mixtures of alkali metal-containing solutions may be prepared also in these ways. The impregnated carriers are then heated to a temperature between about 50° C. and about 600° C., preferably between about 75° C. and about 400° C. to evaporate the liquid and produce a metallic silver.

In general terms, the impregnation process comprises impregnating the support with one or more solutions comprising silver, alkali metal, rare earth, rhenium and rhenium co-promoter. As used in the instant specification and claims, the terminology "impregnating the support with one or more solutions comprising silver, alkali metal, rare earth, rhenium and/or rhenium co-promoter" and similar or cognate terminology means that the support is impregnated in a single or multiple impregnation with one solution containing silver, alkali metal, rare earth, rhenium and rhenium co-promoter in differing amounts; or in multiple impregnations with two or more solutions, wherein each solution contains at least one component selected from silver, alkali metal, rare earth, rhenium and rhenium co-promoter, with the proviso that all of the components of silver, alkali metal, rare earth, rhenium and rhenium co-promoter will individually be found in at least one of the solutions. The concentration of the silver (expressed as the metal) in the silver-containing solution will range from about 1 g/l up to the solubility limit when a single impregnation is utilized. The concentration of the alkali metal (expressed as the metal) will range from about $1 \times 10^{-3}$ g/l up to about 12 g/l and preferably, from about $10 \times 10^{-3}$ g/l to about 12 g/l when a single impregnation step is utilized. The concentration of the rare earth (expressed as the element) will range from about $1 \times 10^{-4}$ g/l up to about 1 g/l and preferably, from about $5 \times 10^{-4}$ g/l to about 0.1 g/l when a single impregnation step is utilized. The concentration of the rhenium (expressed as the metal) will range from about $5 \times 10^{-3}$ g/l to about 20 g/l and preferably from about $50 \times 10^{-3}$ g/l to about 20 g/l when a single impregnation step is utilized. The concentration of rhenium co-promoter (expressed as the element) will range from about $1 \times 10^{-3}$ g/l to about 20 g/l and preferably from about $10 \times 10^{-3}$ g/l to about 20 g/l when a single impregnation step is utilized. Concentrations selected within the above noted ranges will depend upon the pore volume of the catalyst, the final amount desired in the final catalyst and whether the impregnation is single or multiple. Appropriate concentrations can be readily determined by routine experimentation.

The amount of silver deposited on the support or present on the support is to be a catalytically effective amount of silver, i.e., an amount that catalyzes the reaction of ethylene and oxygen to produce ethylene oxide. Preferably this amount will range from about 1 to about 30 percent by weight of the total catalyst, more preferably from about 1 to about 25 percent by weight of the total catalyst, and even more preferably from about 5 to about 20 percent by weight of the total catalyst. The upper and lower limits of preferred silver concentrations can be suitably varied, depending upon the particular catalytic properties or effect desired or the other variables involved. The lower limit of silver is probably about 1 percent by weight of the total catalyst, and the upper limit of silver is probably about 30 percent by weight of the total catalyst.

The amount of alkali metal deposited on the support or catalyst or present on the support or catalyst is to be a promoting amount. Preferably the amount will range from about 10 parts per million to about 3000 parts per million, more preferably from about 15 parts per million to about 2000 parts per million and even more preferably from about 20 parts per million to about 1500 parts per million, and most preferably, from about 50 parts per million to about 1000 parts per million by weight of the total catalyst, expressed as the metal. The upper and lower limits of preferred alkali metal concentrations can be suitably varied depending upon the particular promoting effect desired or other variables involved. A possible lower limit of alkali metal is, for example, about 1 parts per million by weight of the total catalyst, expressed as the metal, and a possible upper limit of alkali metal is, for example, about 3000 parts per million by weight of the total catalyst, expressed as the metal.

The amount of rare earth deposited on the support or catalyst or present on the support or catalyst is to be a promoting amount. Preferably, the amount will range from about 10 parts per million to about 1000 parts per million, preferably from about 15 parts per million to about 500 parts per million, and more preferably, from about 30 parts per million to about 250 parts per million by weight of the total catalyst, expressed as the rare earth element. The upper and lower limits of preferred rare earth concentrations can be suitably varied depending upon the particular promoting effect desired or other variables involved. A possible lower limit of rare earth is, for example, about 1 part per million by weight of the total catalyst, expressed as the rare earth element, and a possible upper limit of rare earth is, for example, about 2,000 parts per million by weight of the total catalyst, expressed as the rare earth element.

The amount of rhenium deposited on the support or catalyst or present on the support of catalyst is to be a promoting amount. Preferably, the amount will range from about 0.1 micromoles per gram to about 10 micromoles per gram, preferably from about 0.2 micromoles per gram to about 5 micromoles per gram, and more preferably, from about 0.5 micromoles per gram to about 4 micromoles per gram of total catalyst, expressed as the metal. The upper and lower limits of preferred rhenium concentrations can be suitably varied depending upon the particular promoting effect desired or other variables involved. A possible lower limit of rhenium is, for example, about 0.01 micromoles per gram of total catalyst, and a possible upper limit of rhenium is, for example, about 16 micromoles per gram of total catalyst, expressed as the metal.

The amount of rhenium co-promoter deposited on the support or catalyst or present on the support or catalyst is to be a promoting amount. Preferably, the amount will range from about 0.1 micromoles per gram to about 10 micromoles per gram, preferably from about 0.2 micromoles per gram to about 5 micromoles per gram, and more preferably, from about 0.5 micromoles per gram to about 4 micromoles per gram of total catalyst, expressed as the element or the metal. The upper and lower limits of preferred rhenium co-promoter concentrations can be suitably varied depending upon the particular promoting effect desired or other variables involved. A possible lower limit of rhenium co-promoter is, for example, about 0.01 micromoles/gram of total catalyst, and a possible upper limit of rhenium co-promoter is, for example, about 16 micromoles/gram of total catalyst, measured as the metal.

It is observed that independent of the form in which the silver is present in the solution before precipitation on the carrier, the term "reduction to metallic silver" is used, while in the meantime often decomposition by heating occurs. We prefer to use the term "reduction", since $Ag^+$ ion is converted into a metallic Ag atom. Reduction times may generally vary from about 0.5 minute to about 8 hours, depending on the circumstances.

The silver catalysts according to the present invention have been shown to have a particularly high selectivity stability for ethylene oxide production in the direct oxidation of ethylene with molecular oxygen to ethylene oxide. The conditions for carrying out such an oxidation reaction in the presence of the silver catalysts according to the present invention broadly comprise those already described in the prior art. This applies, for example, to suitable temperatures, pressures, residence times, diluent materials such as nitrogen, carbon dioxide, steam, argon, methane or other saturated hydrocarbons, to the presence of moderating agents to control the catalytic action, for example, 1-2-dichloroethane, vinyl chloride, ethyl chloride or chlorinated polyphenyl compounds, to the desirability of employing recycle operations or applying successive conversations in different reactors to increase the yields of ethylene oxide, and to any other special conditions which may be selected in processes for preparing ethylene oxide. Pressures in the range of from atmospheric to about 500 psig are generally employed. Higher pressures, however, are not excluded. Molecular oxygen employed as reactant can be obtained from conventional sources. The suitable oxygen charge may consist essentially or relatively pure oxygen, a concentrated oxygen stream comprising oxygen in major amount with lesser amounts of one or more diluents, such as nitrogen and argon, or another oxygen-containing stream, such as air. It is therefore evident that the use of the present silver catalysts in ethylene oxide reactions is in no way limited to the use of specific conditions among those which are known to be effective. For purposes of illustration only, the following table shows the range of conditions that are often used in current commercial ethylene oxide reactor units.

TABLE II

| *GHSV | 1500–10,000 |
|---|---|
| Inlet Pressure | 150–400 psig |
| Inlet Feed | |

TABLE II-continued

| Ethylene | 1–40% |
|---|---|
| $O_2$ | 3–12% |
| Ethane | 0–3% |
| Argon and/or methane and/or nitrogen diluent chlorohydrocarbon moderator | 0.3–20 ppmv total |
| Coolant temperature | 180–315° C. |
| Catalyst temperature | 180–325° C. |
| $O_2$ conversion level | 10–60% |
| EO Production (Work Rate) | 2–16 lbs. EO/cu. ft. catalyst/hr. |

*Cubic feet of gas at standard temperature and pressure passing over one cubic foot of packed catalyst per hour.

In a preferred application of the silver catalysts according to the present invention, ethylene oxide is produced when an oxygen-containing gas is contacted with ethylene in the presence of the present catalysts at a temperature in the range of from about 180° C. to about 330° C. and preferably about 200° C. to about 325° C.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The invention will be illustrated by the following illustrative embodiments which are provided for illustration only and are not intended to limit the scope of the instant invention.

ILLUSTRATIVE EMBODIMENTS

Illustrative Embodiment 1

The following illustrative embodiment describes typical preparative techniques for making the catalysts of the instant invention (and comparative catalysts) and the typical technique for measuring the properties of these catalysts.

Part A: Preparation of stock silver oxalate/ethylenediamine solution for use in catalyst preparation:

1) Dissolve 415 grams (g) of reagent-grade sodium hydroxide in 2340 milliliters (ml) deionized water. Adjust the temperature to 50° C.

2) Dissolve 1699 g of "Spectropure" (high purity) silver nitrate in 2100 ml deionized water. Adjust the temperature to 50° C.

3) Add sodium hydroxide solution slowly to silver nitrate solution with stirring while maintaining a temperature of 50° C. Stir for 15 minutes after addition is complete, and then lower the temperature to 40° C.

4) Insert clean filter wands and withdraw as much water as possible from the precipitate created in step (3) in order to remove sodium and nitrate ions. Measure the conductivity of the water removed and add back as much fresh deionized water as was removed by the filter wands. Stir for 15 minutes at 40° C. Repeat this process until the conductivity of the water removed is less than 90 $\mu$mho/cm. Then add back 1500 ml deionized water.

5) Add 630 g of high-purity oxalic acid dihydrate in approximately 100g increments. Keep the temperature at 40° C. and stir to mix thoroughly. Add the last portion of oxalic acid dihydrate slowly and monitor pH to ensure that pH does not drop below 7.8.

6) Remove as much water from the mixture as possible using clean filter wands in order to form a highly concentrated silver-containing slurry. Cool the silver oxalate slurry to 30° C.

7) Add 699 g of 92 percent weight (%w) ethylenediamine (8% deionized water). Do not allow the temperature to exceed 30° C. during addition.

The above procedure yields a solution containing approximately 27–33%w silver.

Part B: Preparation of impregnation solutions

For Catalyst A (Gd/Re), into a 10 ml beaker is added 0.166 g of $(NH_4)ReO_4$ and approximately 2.0 g of ethylenediamine/$H_2O$ (50/50 by weight), and the mixture is allowed to dissolve with stirring. 0.079 g of $Li_2SO_4 \cdot H_2O$ is dissolved in 1 ml of water in a weighing dish, and then added to the perrhenate solution. 0.3416 g of $LiNO_3$ is dissolved in 2 ml of water and added to the perrhenate solution. The perrhenate/lithium sulfate/lithium nitrate solution is allowed to stir, ensuring complete dissolution. Separately, 0.0839 g of $Gd(OAc)_3 \cdot 4H_2O$ is dissolved in 3 ml of water. Both dopant solutions are then added to 184 g of the above-prepared silver solution (specific gravity=1.556 g/cc), and the resulting solution is diluted with water to a total weight of 204 g. One-fourth of this solution is used to prepare a catalyst. 0.0475 g of CsOH is added to a 51 g portion of the silver oxalate/dopant solution to prepare the final impregnation solution.

For Catalyst B (Ce/Re), the procedure for Catalyst A is followed, except that 0.656 g of $Ce(OAc)_3$ is used in place of $Gd(OAc)_3 \cdot 4H_2O$.

For Catalyst C (Yb/Re), the procedure for Catalyst A is followed, except that 0.0873g of $Yb(OAc)_3$ is used in place of $Gd(OAc)_3 \cdot 4H_2O$.

For Catalyst D (Re only), the procedure for Catalyst A is followed, except that no $Gd(OAc)_3 \cdot 4H_2O$ is added.

Part C: Catalyst impregnation and curing

Catalyst carrier C which is described in Table 1 is a preferred support for the instant invention and is used in the following examples and illustrative embodiments unless otherwise stated.

Approximately 30 g of carrier C are placed under 25 mm vacuum for 3 minutes at room temperature. Approximately 50 g of doped impregnating solution is then introduced to submerge the carrier, and the vacuum is maintained at 25 mm for an additional 3 minutes. At the end of this time, the vacuum is released, and excess impregnating solution is removed from the carrier by centrifugation for 2 minutes at 500 rpm. If the impregnating solution is prepared without monoethanolamine, then the impregnated carrier is then cured by being continuously shaken in a 300 cu. ft./hr. air stream flowing across a cross-sectional area of approximately 3–5 square inches at 250°–270° C. for 5–6 minutes. If significant monoethanolamine is present in the impregnating solution, then the impregnated carrier is cured by being continuously shaken in a 300 cu. ft./hr. air stream at 250° C. for 2.5 minutes, followed by a 100 cu. ft./hr. air stream at 270° C. for 7.5 minutes (all over a cross-section area of approximately 3–5 square inches). The cured catalyst is then ready for testing.

This procedure will yield catalysts on this carrier which contain approximately 13.5%w Ag with the following approximate dopant levels (expressed in parts per million by weight basis the weight of the total catalyst, i.e., ppmw) and which are approximately optimum in cesium for the given silver and rhenium and sulfur levels and support with regard to initial selectivity under the test conditions described below.

|  | Cs, ppmw | Rare Earth, ppmw | Re, ppmw | S, ppmw |
| --- | --- | --- | --- | --- |
| Catalyst A | 460 | 79 | 280 | 48 |
| Catalyst B | 430 | 70 | 280 | 48 |
| Catalyst C | 460 | 86 | 280 | 48 |
| Catalyst D | 430 | None | 280 | 48 |

The actual silver content of the catalyst can be determined by any of a number of standard, published procedures. The actual level of rhenium on the catalysts prepared by the above process can be determined by extraction with 20 mM aqueous sodium hydroxide, followed by spectrophotometric determination of the rhenium in the extract. The actual level of rare earth on the catalyst can be determined by standard atomic emission spectroscopy. The actual level of cesium on the catalyst can be determined by employing a stock cesium hydroxide solution, which has been labeled with a radioactive isotope of cesium, in catalyst preparation. The cesium content of the catalyst can then be determined by measuring the radioactivity of the catalyst. Alternatively, the cesium content of the catalyst can be determined by leaching the catalyst with boiling deionized water. In this extraction process cesium, as well as other alkali metals, is measured by extraction from the catalyst by boiling 10 grams of whole catalyst in 20 milliliters of water for 5 minutes, repeating the above two more times, combining the above extractions and determining the amount of alkali metal present by comparison to standard solutions of reference alkali metals using atomic absorption spectroscopy (using Varian Techtron Model 1200 or equivalent). It should be noted that the cesium content of the catalyst as determined by the water leaching technique may be lower than the cesium content of the catalyst as determined by the radiotracer technique.

Part D: Standard Microreactor Catalyst Test Conditions/Procedure 3 to 5 grams of crushed catalyst (14–20 mesh) are loaded into a ¼ inch diameter stainless steel U-shaped tube. The U tube is immersed in a molten metal bath (heat medium) and the ends are connected to a gas flow system. The weight of the catalyst used and the inlet gas flow rate are adjusted to achieve a gas hourly space velocity of 3300 cc of gas per cc of catalyst per hour. The inlet gas pressure is 210 psig.

The gas mixture passed thorough the catalyst bed (in once-through operation) during the entire test run (including startup) consists of 30% ethylene, 8.5% oxygen, 5% carbon dioxide, 54.5% nitrogen, and 2.0 to 6.0 ppmv ethyl chloride.

The initial reactor (heat medium) temperature is 225° C. After 1 hour at this initial temperature, the temperature is increased to 235° C. for 1 hour, and then adjusted to 245° C. for 1 hour. The temperature is then adjusted so as to achieve a constant oxygen conversion level of 40%. Performance data at this conversion level are usually obtained when the catalyst has been onstream for a total of at least 2–3 days. Due to slight differences in feed gas composition, gas flow rates, and the calibration of analytical instruments used to determine the feed and product gas compositions, the measured selectivity and activity of a given catalyst may vary slightly from one test run to the next. To allow meaningful comparison of the performance of catalysts tested at different times, all catalysts described in this illustrative embodiment were tested simultaneously with a reference catalyst. All performance data reported in this illustrative embodiment are corrected relative to the average initial performance of the reference catalyst ($S_{40}=81.0\%$; $T_{40}=230°$ C.).

After obtaining initial performance values for selectivity at 40% conversion the catalysts are subjected to high severity aging conditions. Under these conditions, the catalyst is brought to either 85% conversion or a maximum of 285° C. for a 10-day period to accelerate the aging of the catalyst. After this 10-day aging period, the catalysts are again brought to 40% conversion and reoptimized under standard conditions. The selectivity is again measured, and compared to the original value of the fresh catalyst. After the new selectivity value is determined, this cycle is repeated, and the selectivity decline of the catalyst is continuously measured under standard 40% conversion conditions in 10-day cycles relative to its fresh initial performance. The results are presented below in Table III. All selectivity values are expressed as %. The initial performances of Catalysts A, B, C and D were determined to be the same, within experimental error. Initial $S_{40}$ values of $86.0\% \pm 0.4\%$ and $T_{40}$ values of $260°$ C. $\pm 3°$ C. were obtained.

Loss is Selectivity (%) = {$S_{40}$, % (Aged)} − {$S_{40}$, % (Fresh)}

TABLE III

Loss of Selectivity from Fresh Catalyst
Total Days at Either 85% conversion or 285° C.
(Data Obtained at 40% Conversion Conditions)

| Catalyst | 10 Days | 20 Days | 30 Days | 40 Days | 50 Days |
|---|---|---|---|---|---|
| A (Re/Gd) | 0% | −0.8% | −1.4% | −2.2% | −3.4% |
| B (Re/Ce) | 0% | 0% | −0.4% | — | — |
| C (Re/Yb) | 0% | — | — | — | — |
| D (Re) | −1.2% | −2.3% | −3.4% | −5.0% | −6.1% |

As mentioned previously, selectivity decline is of tremendous economic importance when choosing a catalyst, and retarding this decline rate can lead to significant savings in costs. As can be seen from Table III, Catalyst D, which does not contain a rare earth element in combination with Re, decreases in selectivity much more rapidly than do the catalysts which contain a rare earth element. Catalysts which contain rare earth elements in combination with rhenium maintain their selectivity significantly longer than catalysts without added rare earth elements and are thus significantly advantaged.

What is claimed is:

1. An ethylene oxide catalyst for the vapor phase production of ethylene oxide from ethylene and oxygen comprising a catalytically effective amount of silver, a promoting amount of an alkali metal or mixtures thereof, a promoting amount of a rare earth metal compound or mixtures thereof and a promoting amount of rhenium supported on a suitable support having a surface area in the range of from about 0.05 m²/g to about 10 m²/g.

2. The catalyst of claim 1 wherein said support comprises a porous refractory oxide.

3. The catalyst of claim 2 wherein the support comprises alpha alumina.

4. The catalyst of claim 3 wherein the support surface area is in the range of from about 0.05 m²/g to about 5 m²/g.

5. The catalyst of claim 1 wherein the amount of silver is in the range of from about 1 percent by weight to about 25 percent by weight of the total catalyst, the amount of alkali metal promoter is in the range of from about 10 parts per million to about 1500 parts per million, expressed as the metal, by weight of the total catalyst, the amount of rare earth promoter is in the range of from about 10 parts per million to about 1000 parts per million, expressed as the rare earth element, by weight of the total catalyst and the amount of rhenium promoter is in the range of from about 0.1 micromoles to about 10 micromoles of rhenium, expressed as the metal, per gram of total catalyst.

6. The catalyst of claim 1 wherein the alkali metal is selected from potassium, rubidium, cesium, lithium and mixtures thereof.

7. The catalyst of claim 6 wherein the alkali metal is potassium.

8. The catalyst of claim 6 wherein the alkali metal is rubidium.

9. The catalyst of claim 6 wherein the alkali metal is cesium.

10. The catalyst of claim 6 wherein the alkali metal comprises cesium plus at least one additional alkali metal.

11. The catalyst of claim 10 wherein the alkali metal is cesium plus potassium.

12. The catalyst of claim 10 wherein the alkali metal is cesium plus rubidium.

13. The catalyst of claim 10 wherein the alkali metal is cesium plus lithium.

14. The catalyst of claim 1 wherein the rare earth metal in the rare earth metal compound is selected from elements 58 through 71 of the Periodic Table of the Elements and mixtures thereof.

15. The catalyst of claim 14 wherein the rare earth metal in the rare earth metal compound is selected from cerium, neodymium, samarium, gadolinium, dysprosium, erbium, ytterbium and mixtures thereof.

16. The catalyst of claim 14 wherein the rare earth metal in the rare earth metal compound is selected from cerium, gadolinium, ytterbium and mixtures thereof.

17. The catalyst of claim 16 wherein the rare earth metal in the rare earth metal compound is gadolinium.

18. The catalyst of claim 16 wherein the rare earth metal in the rare earth metal compound is cerium.

19. The catalyst of claim 16 wherein the rare earth metal in the rare earth metal compound is ytterbium.

20. A catalyst for the vapor phase production of ethylene oxide from ethylene and molecular oxygen comprising silver, an alkali metal promoter, from about 10 parts per million to about 1000 parts per million by weight of the total catalyst of rare earth promoter, expressed as the element, and rhenium promoter supported on a porous refractory support having a surface area in the range of from about 0.05 m²/g to about 10 m²/g[, wherein the rare earth is applied to the support in the form of an oxide or oxygen-bound species].

21. An ethylene oxide catalyst for the vapor phase production of ethylene oxide from ethylene and oxygen comprising a catalytically effective amount of silver, a promoting amount of an alkali metal or mixtures thereof, a promoting amount of a rare earth metal compound or mixtures thereof, a promoting amount of rhenium and a rhenium co-promoter selected from compounds, salts or complexes of sulfur, molybdenum, tungsten, chromium and mixtures thereof supported on a support having a surface area in the range of from about 0.05 m²/g to about 10 m²/g.

22. The catalyst of claim 21 wherein said support comprises a porous refractory oxide.

23. The catalyst of claim 22 wherein the support comprises alpha alumina.

24. The catalyst of claim 23 wherein the support surface area is in the range of from about 0.05 m²/g to about 5 m²/g.

25. The catalyst of claim 21 wherein the amount of silver is in the range of from about 1 percent by weight to about 25 percent by weight of the total catalyst, the amount of alkali metal promoter is in the range of from about 10 parts per million to about 3000 parts per million, expressed as the metal, by weight of the total catalyst, the amount of rare earth metal promoter is in the range of from about 10 parts per million to about 1000 parts per million, expressed as the rare earth element, by weight of the total catalyst, the amount of rhenium promoter is in the range of from about 0.1 micromoles to about 10 micromoles of rhenium, expressed as the metal, per gram of total catalyst and the amount of rhenium co-promoter is in the range of from about 0.1 micromoles to about 10 micromoles of rhenium, expressed as the element, per gram of total catalyst.

26. The catalyst of claim 21 wherein the alkali metal is selected from potassium, rubidium, cesium, lithium and mixtures thereof.

27. The catalyst of claim 26 wherein the alkali metal is potassium.

28. The catalyst of claim 26 wherein the alkali metal is rubidium.

29. The catalyst of claim 26 wherein the alkali metal is cesium.

30. The catalyst of claim 26 wherein the alkali metal is cesium plus at least one additional alkali metal.

31. The catalyst of claim 30 wherein the alkali metal is cesium plus potassium.

32. The catalyst of claim 30 wherein the alkali metal is cesium plus rubidium.

33. The catalyst of claim 30 wherein the alkali metal is cesium plus lithium.

34. The catalyst of claim 21 wherein the rare earth metal in the rare earth metal compound is selected from elements 58 through 71 of the Periodic Table of the Elements and mixtures thereof.

35. The catalyst of claim 34 wherein the rare earth metal in the rare earth metal compound is selected from cerium, neodymium, samarium, gadolinium, dysprosium, erbium, ytterbium and mixtures thereof.

36. The catalyst of claim 34 wherein the rare earth metal in the rare earth metal compound is selected from cerium, neodymium, gadolinium, ytterbium and mixtures thereof.

37. The catalyst of claim 36 wherein the rare earth metal in the rare earth metal compound is gadolinium.

38. The catalyst of claim 36 wherein the rare earth metal in the rare earth metal compound is cerium.

39. The catalyst of claim 36 wherein the rare earth metal in the rare earth metal compound is ytterbium.

40. The catalyst of claim 21 wherein the rhenium co-promoter comprises an oxidic compound or an oxyanion.

41. The catalyst of claim 21 wherein the rhenium co-promoter is selected from sulfate, sulfite, sulfonate, molybdate, tungstate, chromate and mixtures thereof.

42. A catalyst for the vapor phase production of ethylene oxide from ethylene and molecular oxygen comprising silver, an alkali metal promoter, from about 10 parts per million to about 1000 parts per million of rare earth promoter, expressed as the element, a rhenium promoter and a rhenium co-promoter selected from sulfur, molybdenum, tungsten, chromium and mixtures thereof supported on a porous refractory support having a surface area in the range of from about 0.05 m²/g to about 10 m²/g.

43. A process for preparing a catalyst for the vapor phase production of ethylene oxide from ethylene and molecular oxygen which process comprises impregnating a porous refractory oxide with a catalytically effective amount of silver, a promoting amount of an alkali metal or mixture thereof, a promoting amount of a rare earth metal compound or mixtures thereof and a promoting amount of rhenium.

44. The process of claim 43 wherein the alkali metal is selected from potassium, rubidium, cesium, lithium, sodium and mixtures thereof.

45. The process of claim 44 wherein the alkali metal is cesium plus at least one additional alkali metal.

46. The process of claim 43 wherein the rare earth metal in the rare earth metal compound is selected from elements 58 through 71 of the Periodic Table of the Elements and mixtures thereof.

47. The process of claim 46 wherein the rare earth metal in the rare earth metal compound is selected from cerium, neodymium, samarium, gadolinium, dysprosium, erbium, ytterbium and mixtures thereof.

48. The process of claim 46 wherein the rare earth metal in the rare earth metal compound is selected from cerium, gadolinium, ytterbium and mixtures thereof.

49. The process of claim 43 wherein the rare earth metal in the rare earth metal compound is applied to the support in the form of an oxide or an oxygen-bound species.

50. The process of claim 43 wherein the rhenium is applied to the support in the form of a perrhenate or rhenium heptoxide.

51. A process for preparing a catalyst for the vapor phase production of ethylene oxide from ethylene and molecular oxygen which comprising impregnating a porous refractory support with one or more solutions comprising silver, alkali metal, rare earth metal compound and rhenium, wherein the concentration of the silver (expressed as the metal) in the solution ranges from about 1 gram/liter to the solubility limit of silver in the solution, the concentration of alkali metal (expressed as the metal) in the solution ranges from about $1 \times 10^{-3}$ grams/liter to about 12 grams/liter, the concentration of the rare earth metal compound (expressed as the element) in the solution ranges from about $1 \times 10^{-4}$ grams/liter to about 1 gram/liter and the concentration of the rhenium (expressed as the metal) in the solution ranges from about $5 \times 10^{-3}$ grams/liter to about 20 grams/liter to provide the catalyst with a catalytically effective amount of silver, a promoting amount of an alkali metal or mixtures thereof, a promoting amount of rare earth metal compound and a promoting amount of rhenium.

52. The process of claim 51 wherein after impregnation, the silver is reduced to metallic silver.

53. The process of claim 52 wherein after impregnation, the silver is reduced to metallic silver by heating at a temperature between about 50° C. and about 600° C.

54. The process of claim 51 wherein the solution containing silver also comprises water and vicinal alkylenediamine(s) of from 2 to 4 carbon atoms.

55. The process of claim 51 wherein the solution containing silver also comprises water, vicinal alkylenediamine(s) of from 2 to 4 carbon atoms and vicinal alkanolamine(s) of from 2 to 4 carbon atoms.

56. A process for preparing a catalyst for the vapor phase production of ethylene oxide from ethylene and molecular oxygen which comprising impregnating a porous refractory support comprising alpha alumina with one or more solutions comprising solvent having silver compound(s) dissolved therein, alkali metal compound(s) dissolved therein, rare earth metal compound(s) dissolved therein and rhenium compound(s) dissolved therein sufficient to deposit on the support from about 1 percent by weight to about 25 percent by weight of the total catalyst of the silver compound(s), expressed as the metal, from about 10 parts per million to about 3000 parts per million by weight of alkali metal compound(s), expressed as the metal, by weight of the total catalyst, from about 10 parts per million to about 1000 parts per million by weight of the total catalyst of rare earth metal compound(s), expressed as the element, and from about 0.1 micromoles to about 10 micromoles per gram of total catalyst of rhenium compound(s), expressed as the metal, to provide the catalyst with a catalytically effective amount of silver, a promoting amount of alkali metal, a promoting amount of rare earth metal compound and a promoting amount of rhenium.

57. The process of claim 56 wherein after impregnation, the silver is reduced to metallic silver.

58. The process of claim 57 wherein after impregnation, the silver is reduced to metallic silver by heating at a temperature between about 50° C. and about 600° C.

59. The process of claim 56 wherein the silver compound is selected from silver oxalate, silver oxide, silver carbonate, silver lactate and mixtures thereof.

60. The process of claim 56 wherein the alkali metal compound is a hydroxide, sulfate and/or nitrate.

61. The process of claim 56 wherein the rare earth metal compound is a nitrate, oxalate and/or acetate.

62. The process of claim 56 wherein the rhenium-containing compound is ammonium and/or alkali metal perrhenate and/or rhenium heptoxide.

63. A process for preparing a catalyst for the vapor phase production of ethylene oxide from ethylene and molecular oxygen which process comprises impregnating a porous refractory oxide with a catalytically effective amount of silver, a promoting amount of an alkali metal or mixture thereof, a promoting amount of a rare earth metal compound or mixtures thereof, a promoting amount of rhenium and a rhenium co-promoter selected from sulfur, molybdenum, tungsten, chromium and mixtures thereof.

64. The process of claim 63 wherein the alkali metal is selected from potassium, rubidium, cesium, lithium, sodium and mixtures thereof.

65. The process of claim 64 wherein the alkali metal is cesium plus at least one additional alkali metal.

66. The process of claim 63 wherein the rare earth metal in the rare earth metal compound is selected from elements 58 through 71 of the Periodic Table of the Elements and mixtures thereof.

67. The process of claim 66 wherein the rare earth metal in the rare earth metal compound is selected from cerium, neodymium, samarium, gadolinium, dysprosium, erbium, ytterbium and mixtures thereof.

68. The process of claim 66 wherein the rare earth metal in the rare earth metal compound is selected from cerium, gadolinium, ytterbium and mixtures thereof.

69. The process of claim 63 wherein the rare earth metal in the rare earth metal compound is applied to the support in the form of an oxide or an oxygen-bound species.

70. The process of claim 63 wherein the rhenium is applied to the support in the form of a perrhenate or rhenium heptoxide.

71. A process for preparing a catalyst for the vapor phase production of ethylene oxide from ethylene and molecular oxygen which comprising impregnating a porous refractory support with one or more solutions comprising silver, alkali metal, rare earth metal compound, rhenium and rhenium co-promoter, wherein the concentration of the silver (expressed as the metal) in the solution ranges from about 1 gram/liter to the solubility limit of silver in the solution, the concentration of alkali metal (expressed as the metal) in the solution ranges from about $1 \times 10^{-3}$ grams/liter to about 12 grams/liter, the concentration of the rare earth metal compound (expressed as the element) in the solution ranges from about $1 \times 10^{-5}$ grams/liter to about 1 gram/liter, the concentration of the rhenium (expressed as the metal) in the solution ranges from about $5 \times 10^{-3}$ grams/liter to about 20 grams/liter and the concentration of the rhenium co-promoter (expressed as the element) in the solution ranges from about $1 \times 10^{-3}$ grams/liter to about 20 grams/liter to provide the catalyst with a catalytically effective amount of silver, a promoting amount of an alkali metal or mixture thereof, a promoting amount of rare earth metal compound or mixtures thereof, a promoting amount of rhenium, and a promoting amount of rhenium co-promoter.

72. The process of claim 71 wherein after impregnation, the silver is reduced to metallic silver.

73. The process of claim 72 wherein after impregnation, the silver is reduced to metallic silver by heating at a temperature between about 50° C. and about 600° C.

74. The process of claim 71 wherein the solution containing silver also comprises water and vicinal alkylenediamine(s) of from 2 to 4 carbon atoms.

75. The process of claim 71 wherein the solution containing silver also comprises water, vicinal alkylenediamine(s) of from 2 to 4 carbon atoms and vicinal alkanolamine(s) of from 2 to 4 carbon atoms.

76. A process for preparing a catalyst for the vapor phase production of ethylene oxide from ethylene and molecular oxygen which comprising impregnating a porous refractory support comprising alpha alumina with one or more solutions comprising solvent having silver compound(s) dissolved therein, alkali metal compound(s) dissolved therein, rare earth metal compound(s) dissolved therein and rhenium compound(s) dissolved therein sufficient to deposit on the support from about 1 percent by weight to about 25 percent by weight of the total catalyst of the silver compound(s), expressed as the metal, from about 10 parts per million to about 3000 parts per million by weight of alkali metal compound(s), expressed as the metal, by weight of the total catalyst, from about 10 parts per million to about 1000 parts per million by weight of the total catalyst of rare earth metal compound(s), expressed as the element, from about 0.1 micromoles to about 10 micromoles per gram of total catalyst of rhenium compound(s), expressed as the metal, and from about 0.1 micromoles to about 10 micromoles per gram of total catalyst of rhenium co-promoter compound(s), expressed as the element, to provide the catalyst with a catalytically effective amount of silver, a promoting amount of an alkali metal or mixture thereof, a promoting amount of rare earth metal compound or mixtures thereof, a promoting amount of rhenium and a promoting amount of rhenium co-promoter.

77. The process of claim 76 wherein after impregnation, the silver is reduced to metallic silver.

78. The process of claim 77 wherein after impregnation, the silver is reduced to metallic silver by heating at a temperature between about 50° C. and about 600° C.

79. The process of claim 76 wherein the silver compound is selected from silver oxalate, silver oxide, silver carbonate, silver lactate and mixtures thereof.

80. The process of claim 76 wherein the alkali metal compound is a hydroxide, sulfate and/or nitrate.

81. The process of claim 76 wherein the rare earth metal compound is a nitrate, oxalate and/or acetate.

82. The process of claim 76 wherein the rhenium-containing compound is ammonium and/or alkali metal perrhenate and/or rhenium heptoxide.

83. The process of claim 76 wherein the rhenium co-promoter compound is selected from compounds of sulfur, tungsten, molybdenum, chromium and mixtures thereof.

84. The process of claim 83 wherein the sulfur compound is selected from ammonium sulfate, alkali metal sulfate and mixtures thereof, the tungsten compound is selected from ammonium tungstate, alkali metal tungstate, tungstic acid and mixtures thereof, the molybdenum compound is selected from ammonium molybdate, alkali metal molybdate, molybdic acid and mixtures thereof and the chromium compound is selected from ammonium chromate, alkali metal chromate, dichromate, chromic acid, dichromic acid and mixtures thereof.

* * * * *